United States Patent
Alagappan et al.

(10) Patent No.: US 8,797,030 B2
(45) Date of Patent: Aug. 5, 2014

(54) MAGNETIC RESONANCE RADIO-FREQUENCY COIL AND METHOD OF MANUFACTURING

(75) Inventors: Vijayanand Alagappan, Streetsboro, OH (US); Victor Taracila, Beachwood, OH (US); Fraser Robb, Aurora, OH (US)

(73) Assignee: General Electric Company, Schenectady, NY (US)

( * ) Notice: Subject to any disclaimer, the term of this patent is extended or adjusted under 35 U.S.C. 154(b) by 363 days.

(21) Appl. No.: 13/193,165

(22) Filed: Jul. 28, 2011

(65) Prior Publication Data

US 2013/0027040 A1 Jan. 31, 2013

(51) Int. Cl.
*G01V 3/00* (2006.01)
(52) U.S. Cl.
USPC .......................................... 324/307; 324/322
(58) Field of Classification Search
USPC .................................................. 324/300–322
See application file for complete search history.

(56) References Cited

U.S. PATENT DOCUMENTS

| 4,939,464 | A | * | 7/1990 | Hammer | 324/318 |
| 7,394,254 | B2 | | 7/2008 | Rieke et al. | |
| 7,714,577 | B2 | * | 5/2010 | Viswanathan | 324/318 |
| 7,719,278 | B2 | | 5/2010 | Viswanathan | |
| 2008/0169811 | A1 | | 7/2008 | Viswanathan | |
| 2010/0264927 | A1 | | 10/2010 | Viswanathan | |

* cited by examiner

*Primary Examiner* — Dixomara Vargas
(74) *Attorney, Agent, or Firm* — The Small Patent Law Group; Dean D. Small (57) ABSTRACT

A Magnetic Resonance (MR) Radio-Frequency (RF) coil and method of manufacturing are provided for a multi-modality imaging system. The multi-modality imaging system includes a Magnetic Resonance (MR) scanner portion configured to acquired MR data of a patient using one or more MR Radio-Frequency (RF) coils. The one or more MR RF coils are formed from carbon nanotube conductors. The multi-modality imaging system also includes a radiation potion configured to transmit radiation through or detect radiation from the patient.

19 Claims, 6 Drawing Sheets

MAGNETIC RESONANCE RADIO-FREQUENCY COIL AND METHOD OF MANUFACTURING

BACKGROUND OF THE INVENTION

The subject matter disclosed herein relates generally to diagnostic imaging systems, and more particularly to Magnetic Resonance (MR) Radio-Frequency (RF) coils for diagnostic imaging systems.

Magnetic Resonance Imaging (MRI) systems and Nuclear Magnetic Resonance (NMR) imaging systems often include a superconducting magnet that generates a temporally constant (i.e., uniform and static) primary or main, magnetic field. MRI data acquisition is accomplished by exciting magnetic moments within the primary magnetic field using magnetic gradient coils. For example, in order to image a region of interest, the magnetic gradient coils are sequentially pulsed to create pulsed magnetic gradient fields in a bore of an MRI scanner to selectively excite a volume corresponding to the region of interest in order to acquire MR images of the region of interest. The resultant image that is generated shows the structure and function of the region of interest.

In these systems, RF coils, which may be transmit coils, receive coils or transmit and receive coils, are used to acquire the image information of the region of interest of a scanned object. For example, it is known to use a phased array configuration for RF coils in MRI, such as a surface phased array having multiple loop element coils, to receive NMR signals.

When using RF coils in multi-modality system, for example, when using MRI in combination with X-ray Computed Tomography (CT) or Positron Emission Tomography (PET), the RF coils can cause attenuation in the X-rays, transmitted by the CT system or the emissions received by the PET system. The attenuation of the signals can reduce the quality of images subsequently reconstructed. In order to overcome the attenuation, a higher X-ray or radiopharmaceutical dose may be used, which is undesirable, as it exposes the patient to higher levels of X-ray or radioactive isotopes that can be harmful. As a result, the MRI coils are often modified, such as to be more sparsely positioned, so that additional dose is not needed or reduced. However, this arrangement affects the overall system performance, for example, in the quality of images acquired.

BRIEF DESCRIPTION OF THE INVENTION

In accordance with one embodiment, a multi-modality imaging system is provided that includes a Magnetic Resonance (MR) scanner portion configured to acquire MR data of a patient using one or more MR Radio-Frequency (RF) coils. The one or more MR RF coils are formed from carbon nanotube conductors. The multi-modality imaging system also includes a radiation potion configured to transmit radiation through or detect radiation from the patient In accordance with another embodiment, a multi-modality imaging system is provided that includes a first modality having one or more carbon nanotube conductors shaped and sized for operation in MR imaging. The multi-modality imaging system also includes a second modality configured to transmit radiation through or detect radiation that passes through the one or more nanotube conductors.

In accordance with yet another embodiment, a method for forming Magnetic Resonance (MR) Radio-Frequency (RF) coils is provided. The method includes forming nanotube structures having MR imaging properties and forming a nanotube conductor arrangement from the nanotube structures. The method also includes forming MR RF coils, from the nanotube conductor arrangement for use in a multi-modality imaging system having (i) a Magnetic Resonance (MR) scanning portion configured to acquired MR data of a patient using the MR RF coils and (ii) a radiation potion configured to transmit radiation through or detect radiation from the patient.

DETAILED DESCRIPTION OF THE INVENTION

The foregoing summary, as well as the following detailed description of certain embodiments, will be better understood when read in conjunction with the appended drawings. To the extent that the figures illustrate diagrams of the functional blocks of various embodiments, the functional blocks are not necessarily indicative of the division between hardware or circuitry. Thus, for example, one or more of the blocks may be implemented in a single piece of hardware or multiple pieces of hardware. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Various embodiments provide one or more coils, in particular, Magnetic Resonance (MR) Radio-Frequency (RF)

coils for use in imaging systems, such as diagnostic imaging systems. The MR RF coils are formed in various embodiments to have reduced radiation attenuation characteristics or properties (e.g., radiation invisible or transparent coils). As used herein, radiation invisible or transparent generally means that the MR RF coils have reduced or no radiation attenuation characteristics or properties, such that, for example, X-rays or gamma rays are not attenuated by or minimally attenuated by the radiation invisible coils, such that clinically relevant information may be acquired. For example, in one embodiment, the MR RF coils are formed such that the radiation attenuation characteristics or properties are less than MR RF coils formed from copper.

It should be noted that although the various embodiments of MR RF coils may be described in connection with a particular imaging system, such as multi-modality or hybrid imaging system, the various embodiments may be used in connection with any system that, for example, uses gamma or X-ray radiation in combination with MR. Thus, the various embodiments may be used, for example, in a Positron Emission Tomography (PET)/Magnetic Resonance Imaging (MRI) system, a Single Photon Emission Computed Tomography (SPECT)/MRI system, a MR-guided radiotherapy system, a MR/X-ray fluoroscopy system, among others.

Figure 1:
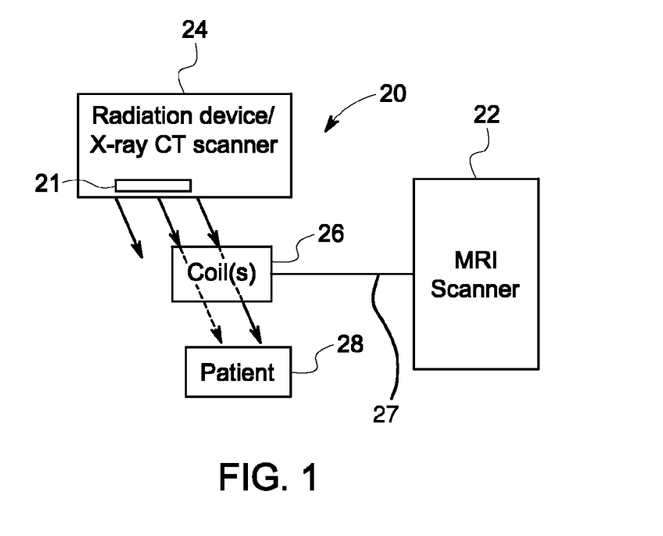
FIG. 1 is a simplified block diagram of a multi-modality imaging system formed in accordance with various embodiments.
Figure 2:
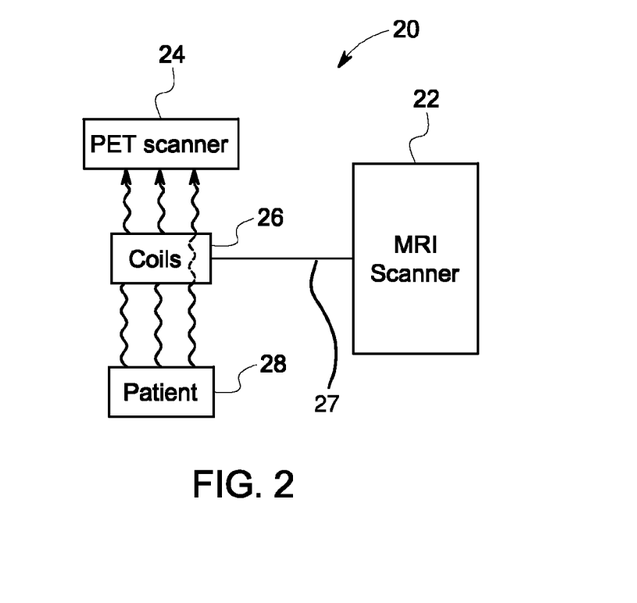
FIG. 2 is a simplified block diagram of a multi-modality imaging system formed in accordance with other various embodiments.

For example, FIGS. 1 and 2 illustrate embodiments of a system in which one or more embodiments of an MR RF coil may be used. The imaging system 20 shown in FIG. 1 includes an MRI scanner portion, illustrated as an MRI scanner 22 that defines a first imaging modality. A second modality 24, which in this embodiment uses X-ray, may be, for example, a radiation device (e.g., a radiation therapy device) or a X-ray imaging device (e.g., an X-ray CT scanner) that includes an X-ray radiation source 21 (e.g., an X-ray tube). Thus, the imaging system 20 is a multi-modality or hybrid imaging system wherein one of the imaging modalities is MR.

The MRI scanner 22 is connected to one or more coils 26, which in this embodiment are MR RF coils, via a link 27 (e.g., a transmission line). The coils 26 may be MR transmit coils, MR receive coils or MR transmit and receive coils. For example, the coils 26 may be a surface or body coil, such as an array of MR RF coils connected to the MRI scanner 22. The coils 26 operate to acquire MR data from a patient 28 as described in more detail herein. Additionally, the second modality 24 is configured to use X-ray radiation in proximity to the coils 26 to provide, for example, radiation therapy to the patient 28 or acquire X-ray attenuation data of the patient 28.

The imaging system 20 shown in FIG. 2 again includes an MRI scanning portion, illustrated as the MRI scanner 22 that defines a first imaging modality. A second modality 24, which in this embodiment detects gamma radiation, is provided, and may be, for example, a PET scanner. Thus, the imaging system 20 is a multi-modality or hybrid imaging system wherein one of the imaging modalities is again MR.

The MRI scanner 22 is connected to the one or more coils 26, which in this embodiment are MR RF coils. The-coils 26 may be MR transmit coils, MR receive coils or MR transmit and receive coils. For example, the coils 26 may be a surface or body coil, such as an array of MR RF coils connected to the MRI scanner 22. The coils 26 operate to acquire MR data from the patient 28 as described in more detail herein. Additionally, the second modality 24 is configured to detect gamma ray radiation in proximity to the coils 26 to provide, for example, PET data of the patient 28.

In various embodiments, the coils 26 are formed to reduce the attenuation of ionizing radiations, such as radiation used by the second modality 24. The coils 26 may have reduced radiation attenuation characteristics or properties, or may be radiation invisible, such that, for example, clinically relevant MR and X-ray data may be acquired by the multi-modality system. For example, in various embodiments, the coils 26 are formed from carbon nanotube based conductors, such as carbon nanotube based ballistic conductors. Thus, an electron injected at one end of the conductor will emerge at the other end without or with reduced backscattering.

Figure 3:
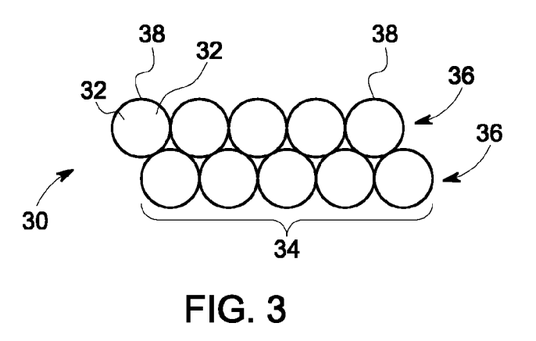
FIG. 3 is a cross-sectional diagrammatic view of a carbon nanotube conductor arrangement formed in accordance with various embodiments.

For example, as illustrated in FIG. 3, a carbon nanotube conductor arrangement 30 (a portion of which is shown) that may be used to form the coils 26 includes a plurality of carbon nanotubes 32 provided in a plurality of bundles 34. It should be, noted that the carbon nanotubes 32 are only shown in one of the bundles 34, but are used to form all of the bundles 34. It should be noted that the number, size and arrangement of the nanotubes 32 and the bundles 34 may be modified as desired or needed, for example, based on the type or configuration of coils 26 to be formed. Thus, the bundles 34 may be provided, such that the carbon nanotube conductor arrangement 30 is sized and shaped dimensionally to form the coils 26 for MR imaging. The bundles 34 optionally may be coupled together and combined in multiple layers 36 to form a sheet that is shaped or cut into and form the body of the coils 26. In one embodiment, 400-500 bundles 34 are used and that are defined by strands 38 that are arranged in parallel (which may include multiple layers 36) such that a resistance of the carbon nanotube conductor arrangement 30 is compatible and can receive excitation signals from an MRI system, such as an MR current.

Figure 4:
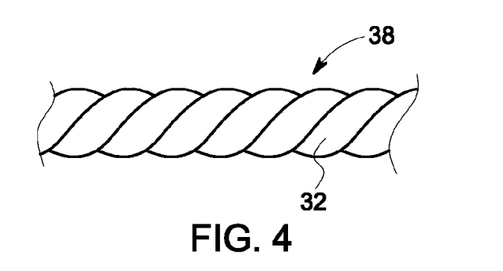
FIG. 4 is a side view of carbon nanotube strand formed in accordance with various embodiments.

In one embodiment, the strands 38 are formed in a twisted arrangement as shown in FIG. 4. For example, the strands 38 may be formed by twisting the nanotubes 32 such as in a yarn-type configuration, for example, having an s-type twist pattern or a z-type twist pattern. The nanotubes 32, thus, may be twisted together in opposite directions as shown. However, it should be noted that more than two nanotubes 32 may be twisted together to form the strand 38. Additionally, the bundles 34 may be formed from single strands 38 or multiple strands 38.

The strands 38 then may be coupled together to form a sheet. The strands 38 may be bundled together and optionally layered using any suitable methods. Different types of nanotube yarn or sheets also may be used in various embodiments. One type of nanotube yarn or sheets is available, for example, from Nanocomp Technologies of Concord, N.H. However, different arrangements and configurations are contemplated. For example, any type of carbon nanotube based material, such as any type of carbon nanotube based conductive yarn or sheet may be used. Thus, by practicing various embodiments, coils 26 formed from materials having lower atomic numbers than copper (e.g., carbon with a Z value of 6) and lower attenuation coefficients than copper, have reduced attenuation to ionizing radiations. Additionally, in embodiments using carbon nanotubes 32, the coils 26 also have an increased flexibility.

Figure 5:
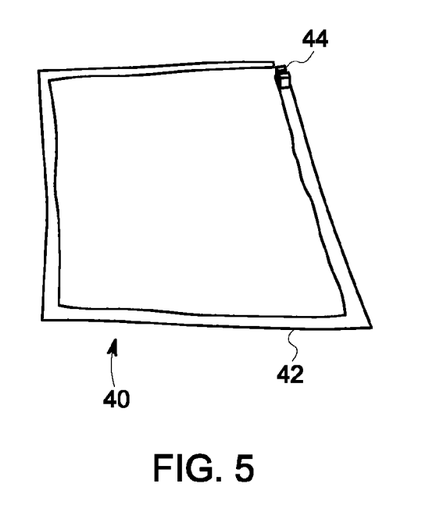
FIG. 5 is a diagram of Magnetic Resonance (MR) coil formed in accordance with one embodiment.
Figure 6:
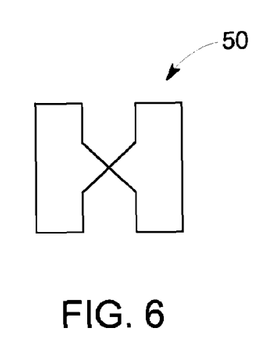
FIG. 6 is a diagram of an MR coil formed in accordance with another embodiment.
Figure 7:
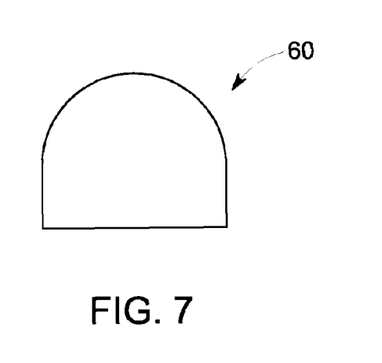
FIG. 7 is a diagram of an MR coil formed in accordance with another embodiment.
Figure 8:
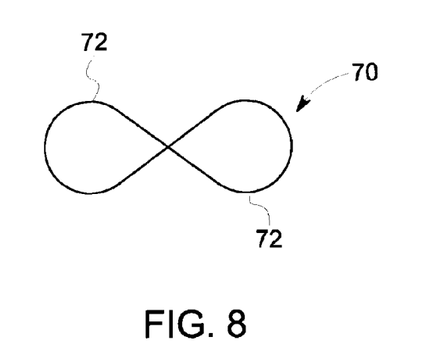
FIG. 8 is a diagram of an. MR coil formed in accordance with another embodiment.
Figure 9:
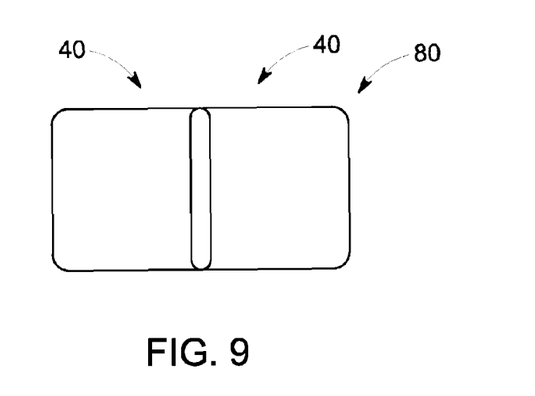
FIG. 9 is a diagram of an MR coil formed in accordance with another embodiment.

The carbon nanotube conductor arrangement 30 in various embodiments is dimensionally sized and shaped to form the body or elements of the conductors for the coils 26. For example, different configurations and shapes of coils 26 may be formed from the carbon nanotube conductor arrangement 30. In one embodiment, a loop coil 40 is formed from carbon nanotube conductor legs 42 as shown in FIG. 5. In other embodiments, a saddle coil 50 as shown in FIG. 6, a solenoid coil 60 as shown in FIG. 7 or a "Figure-8" coil 70 formed from two loops 72 as shown in FIG. 8 may be provided. However, any type or shape of coil may be provided, as well as any arrangement of coils. For example, a coil array 80 may be provided, which is formed from two loop coils 40 (shown in an overlapping arrangement) as shown in FIG. 9.

Additionally, other components may be added to the various coils. For example, as shown in FIG. 4 one or more capacitors 44 (one is shown) may be connected to the coil 40. The capacitor 44 may be coupled to one or more of the legs 42 using, for example, a conductive epoxy or paste.

It should be noted that other components of the imaging system 20 may be formed from carbon nanotubes as described herein with respect to the coils. For example, the link 27 (shown in FIGS. 1 and 2) similarly may be formed from carbon nanotubes using any suitable method and also as described herein. In some embodiments, a carbon nanotube transmission line, such as a carbon nanotube based coaxial cable (e.g., RF coaxial cable) may be used that is formed from carbon nanotube wire and/or tape, which is available, for example, from Nanocomp Technologies of Concord, N.H.

Figure 10:
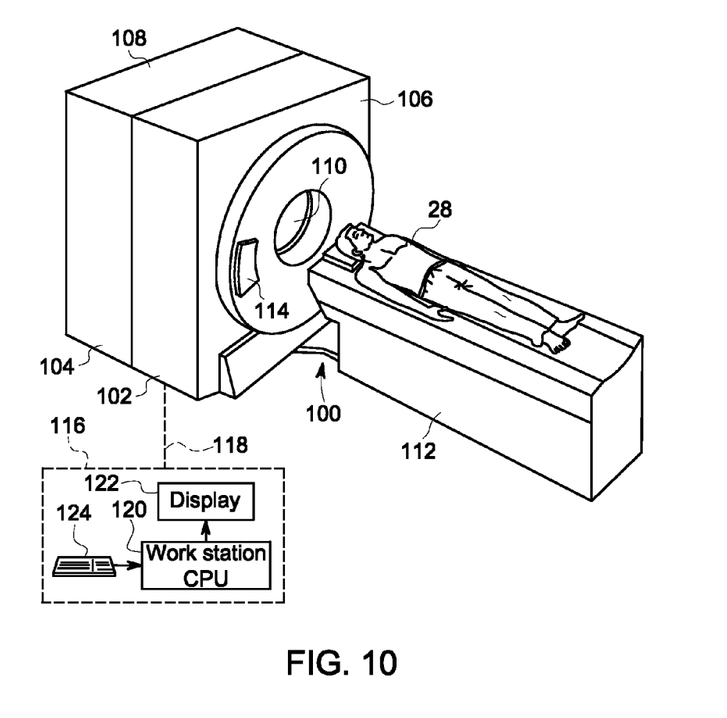
FIG. 10 is perspective view of a multi-modality imaging system formed in accordance with various embodiments.

It should be noted that the various embodiments may be provided as part of a multi-modality system 100 as shown in FIG. 10. The multi-modality imaging system 100 may be any type imaging system, for example, different types of medical imaging systems, which in various embodiments is an MRI system in combination with one of, for example, a PET system, a SPECT system, a CT system, an ultrasound system, or any other system, for example, capable of generating diagnostic images. Moreover, the various embodiments are not limited to medical imaging systems for imaging human subjects, but may include veterinary or non-medical systems for imaging non-human objects, etc., as well as non-imaging applications, such as radiation therapy.

Referring to FIG. 10, the multi-modality imaging system 100 includes a first modality unit 102 and a second modality unit 104. The two modality units enable the Multi-modality imaging system 100 to scan an object or patient 28 in a first modality using the first modality unit 102, which in this embodiment is MR and to scan the patient 28 in a second modality using the second modality unit 104. The multi-modality imaging system 100 allows for multiple scans in different modalities to facilitate an increased diagnostic capability over single modality systems. In one embodiment, the multi-modality imaging system 100 is an MR/CT imaging system and in another embodiment the multi-modality imaging system 100 is an MR/PET imaging system.

The imaging system 100 is shown as including a gantry 106 that is associated with the first modality unit 102, which is an MR scanner and a gantry 108 that is associated with the second modality unit 104, which may be, for example, any system using or detecting X-ray radiation or, gamma radiation. During operation, the patient 28 is positioned within a central opening 110, defined through the imaging system 100, using, for example, a motorized table 112.

The gantry 106 includes MR imaging components, for example, one or more magnets 114 as described in more detail herein. The gantry 108 includes imaging components for an X-ray radiation or gamma radiation type system (e.g., an x-ray tube and detector or gamma emission detectors or cameras, such as Cadmium. Zinc Telluride (CZT) detector modules).

The imaging system 100 also includes an operator workstation 116. During operation, the motorized table 112 moves the patient 28 into the central opening 110 of the gantry 106 and/or 108 in response to one or more commands received from the operator workstation 116. The workstation 116 then operates the first and second modality units 102 and 104 to, for example, both scan the patient 28 in MR and acquire attenuation and/or emission data of the patient 28. The workstation 116 may be embodied, as a personal computer (PC) that is positioned near the imaging system 100 and hardwired to the imaging system 100 via a communication link 118. The Workstation 116 may also be embodied as a portable computer such as a laptop computer or a hand-held computer that transmits information to, and receives information from, the imaging system 100. Optionally, the communication link 118 may be a wireless communication link that enables information to be transmitted to or from the workstation 116 to the imaging system 100 wirelessly. In operation, the workstation 116 is configured to control the operation of the imaging system 100 in real-time. The workstation 116 is also programmed to perform medical image diagnostic acquisition and reconstruction processes described herein.

The operator workstation 116 includes a central processing unit (CPU) or computer 120, a display 122, and an input device 124. In the exemplary embodiment, the computer 120 executes a set of instructions that are stored in one or more storage elements or memories, in order to process information received from the first and second modality units 102 and 104. The storage elements may also store data or other information as desired or needed. The storage element may be in the form of an information source or a physical memory element located within the computer 120. The set of instructions may include various commands that instruct the computer 120 as a processing machine to perform specific operations such as the methods and processes of the various embodiments described herein.

The computer 120 connects to the communication link 118 and receives inputs, e.g., user commands, from the input device 124. The input device 124 may be, for example, a keyboard, mouse, a touch-screen panel, and/or a voice recognition system, etc. Through the input device 124 and associated control panel switches, the operator can control the operation of the first and second modality units 102 and 104 and the positioning of the patient 28 for a scan. Similarly, the operator can control the display of the resulting image on the display 122.

Figure 11:
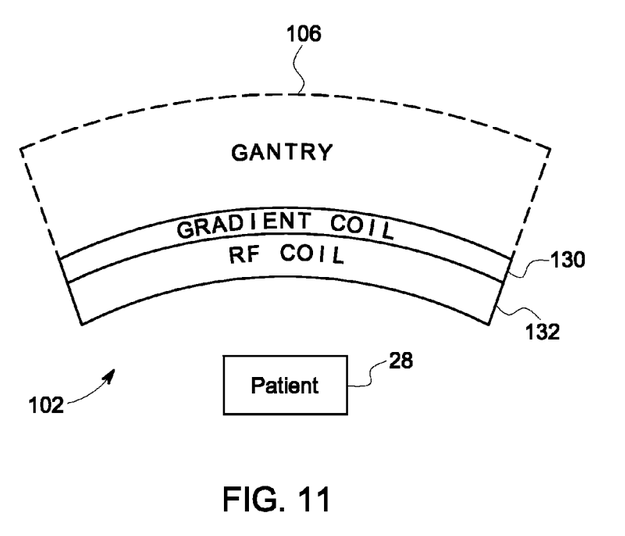
FIG. 11 is a simplified diagram of a portion of an MR scanner formed in accordance with various embodiments.

As shown in FIG. 11, the first modality unit 102 includes the gantry 106 that supports various components of the MR imaging scanner. In this simplified block diagram, the gantry 106 supports one or more gradient coils 130 and one or more RF coils 132, which in various embodiments are formed from the coils 26 as described herein.

Thus, various embodiments provide coils that have reduced radiation attenuation characteristics Or properties such that the attenuation of ionizing radiation therethrough is reduced. For example, the coils 26 may be provided as part of an imaging system 140 as shown in FIG. 12, which is an MRI system that may be embodied as the first imaging modality units 102.

Figure 12:
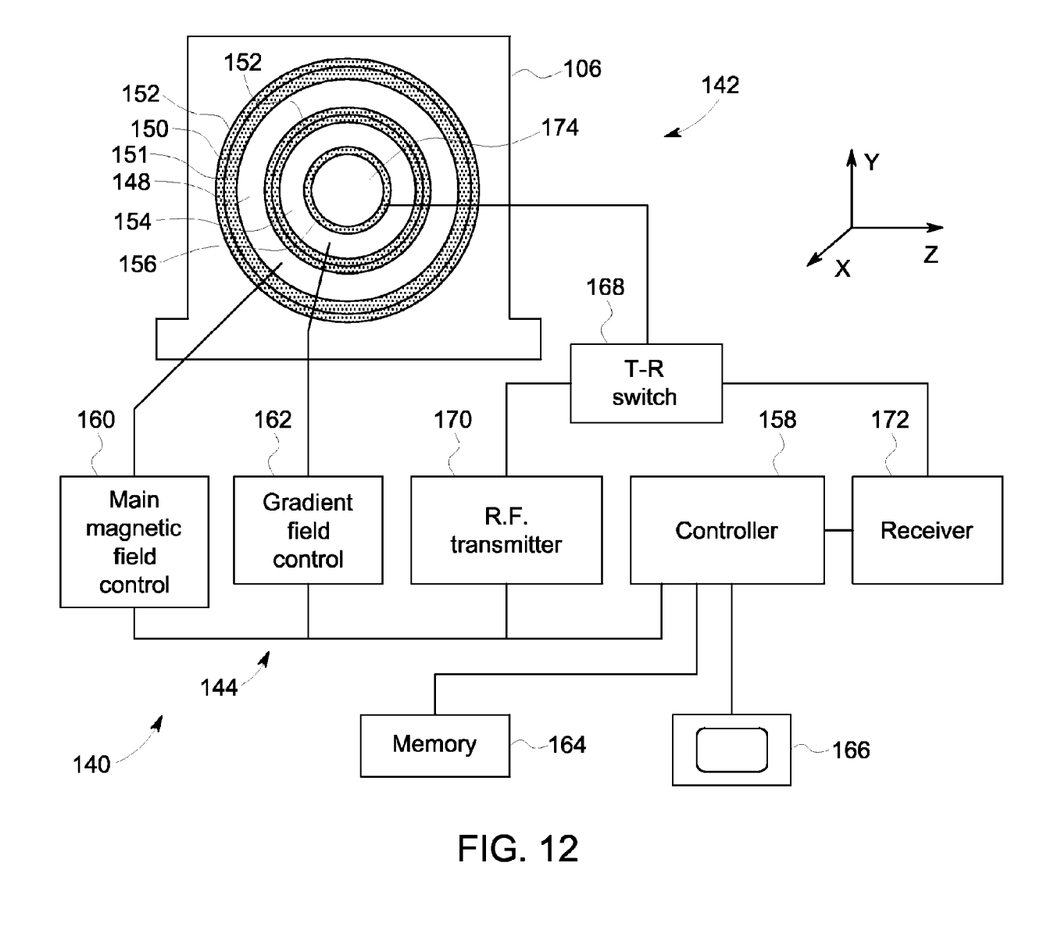
FIG. 12 is a block diagram of a Magnetic Resonance Imaging (MRI) system formed in accordance with various embodiments.

Referring to FIG. 12, the imaging system 140 includes an imaging portion. 142 and a processing portion 144 that may also include a processor or other computing or controller device, such as illustrated in FIG. 11. The MRI system 140 includes within a helium vessel 151 a superconducting magnet 148 formed from coils, which may be supported on a magnet coil support structure. The helium vessel 151 surrounds the superconducting magnet 148 and is filled with liquid helium.

Thermal insulation 152 is provided surrounding all or a portion of the outer surface of the helium vessel 151. A plurality of magnetic gradient coils 154 are provided inside the superconducting magnet 148 and an RF transmit coil. 156 is provided within the plurality of magnetic gradient coils 154, which are formed in various embodiments from carbon nanotube conductors as described herein. In some embodiments, the RF transmit coil 156 may be replaced with a transmit and receive coil. The components within the gantry 150 generally form the imaging portion 142. It should be noted that although the superconducting magnet 148 is a cylindrical shape, other shapes of magnets can be used.

The processing portion 144 generally includes a controller 158, a main magnetic field control 160, a gradient field control 162, a memory 165, a display device, embodied as the monitor 166, a transmit-receive (T-R) switch 168, an RF transmitter 170 and a receiver 172.

In operation, a body of an object, such as a patient or a phantom to be imaged, is placed in a bore 174 on a suitable support, for example, a patient table. The superconducting magnet 148 produces a uniform and static main magnetic field $B_o$ across the bore 174. The strength of the electromagnetic field in the bore 174 and correspondingly in the patient, is controlled by the controller 158 via the main magnetic field control 160, which also controls a supply of energizing current to the superconducting magnet 148.

The magnetic gradient coils 154, which include one or more gradient coil elements, are provided so that a magnetic gradient can be imposed on the magnetic field $B_o$ in the bore 174 within the superconducting magnet 148 in any one or more of three orthogonal directions x, y, and z. The magnetic gradient coils 154 are energized by the gradient field control 162 and are also controlled by the controller 158.

The RF transmit coil 156, which may include a plurality of coils, is arranged to transmit magnetic pulses and/or optionally simultaneously detect MR signals from the patient if receive coil elements are also provided, such as a surface coil configured as an RF receive coil. The RF receive coil may be of any type or configuration, for example, a separate receive surface coil. The receive surface coil may be an array of RF coils provided within the RF transmit coil 156.

The RF transmit coil 156 and the receive surface coil are selectably interconnected to one of the RF transmitter 170 or receiver 172, respectively, by the T-R switch 168. The RF transmitter 170 and T-R switch 168 are controlled by the controller 158 such that RF field pulses or signals are generated by the RF transmitter 170 and selectively applied to the patient for excitation of magnetic resonance in the patient. While the RF excitation pulses are being applied to the patient, the T-R switch 168 is also actuated to disconnect the receive surface coil from the receiver 172.

Following application of the RF pulses, the T-R switch 168 is again actuated to disconnect the RF transmit coil 156 from the RF transmitter 170 and to connect the receive surface coil to the receiver 172. The receive surface coil operates to detect or sense the MR signals resulting from the excited nuclei in the patient and communicates the MR signals to the receiver 172. These detected MR signals are in turn communicated to the controller 158. The controller 158 includes a processor (e.g., image reconstruction processor), for example, that controls the processing of the MR signals to produce signals representative of an image of the patient.

The processed signals representative of the image are also transmitted to the monitor 166 to provide a visual display of the image. Specifically, the MR signals fill or form a k-space that is Fourier transformed to obtain a viewable image. The processed signals representative of the image are then transmitted to the monitor 166.

Figure 13:
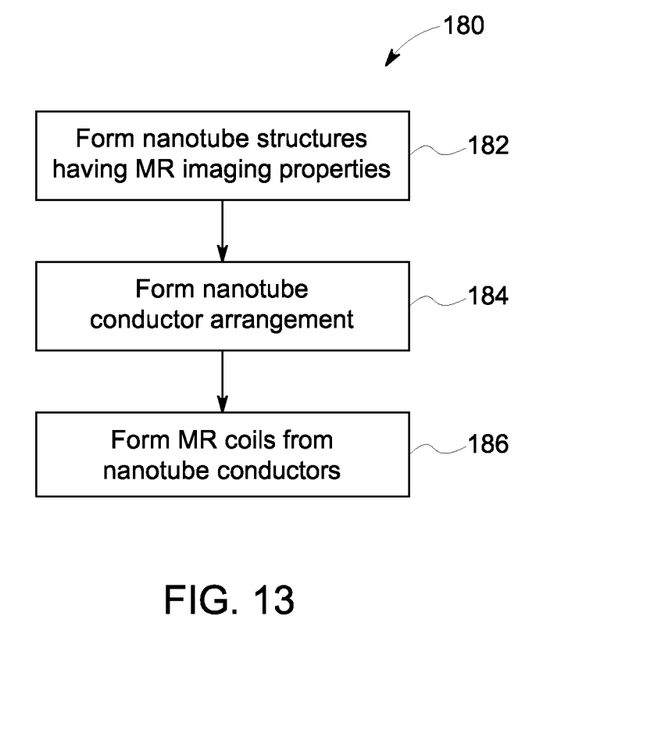
FIG. 13 is a flowchart of a method for forming MR coils in accordance with various embodiments.

Various embodiments also include a method 180 as shown in FIG. 13 for forming MR RF coils. In particular, the method 180 includes forming nanotube structures having MR imaging properties at 182. For example, multiple strands of nanotubes may be formed from twisting the nanotubes. The strands then may be coupled and/or layered together to have a resistance for receiving MR pulses and generating MR signals.

Thereafter, a nanotube conductor arrangement is formed at 184, for example, by cutting the nanotube structures. The cutting of the nanotube structures may be performed using any suitable carbon cutting technique, such as with knives or abrasive cutting wheels. The nanotube conductor arrangement defines, for example, are sized and shaped to define portions of an MR RF coil. The MR-RF coils are then formed at 186 from the nanotube conductors. For example, the nanotube conductors form a loop coil for MR imaging.

The various embodiments and/or components, for example, the modules, or components and controllers therein, such as of the MRI system 140, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as an optical disk drive, solid state disk drive (e.g., flash RAM), and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a, processing machine.

The set of instructions may include various commands that instruct the computer or processor as a processing machine to perform specific operations such as the methods and processes of the various embodiments of the invention. The set of instructions may be in the form of a software program, which may form part of a tangible non-transitory computer readable medium or media. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" may include, any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal languages of the claims.

What is claimed is:

1. A multi-modality imaging system comprising:
   a Magnetic Resonance (MR) scanner portion configured to acquire MR data of a patient using one or more MR Radio-Frequency (RF) coils, the one or more MR RF coils formed from carbon nanotube conductors; and
   a radiation portion configured to transmit radiation through or detect radiation from the patient, wherein the carbon nanotube conductors are configured to allow ionizing radiations from the radiation portion to pass therethrough.

2. The multi-modality imaging system of claim 1, wherein the radiation comprises X-ray radiation transmitted from an X-ray radiation source of the radiation portion.

3. The multi-modality imaging system of claim 1, wherein the radiation comprises gamma radiation emitted as gamma rays from the patient.

4. The multi-modality imaging system of claim 1, wherein the radiation portion comprises one of a Computed Tomography (CT) scanner, a Positron Emission. Tomography (PET) scanner, a Single-Photon Emission Computed Tomography (SPECT) scanner, a radiotherapy system, or an X-ray fluoroscopy system.

5. The multi-modality imaging system of claim 1, wherein the carbon nanotube conductors comprise carbon nanotube based ballistic conductors.

6. The multi-modality imaging system of claim 1, wherein the carbon nanotube conductors comprise bundled strands of carbon nanotube conductors.

7. The multi-modality imaging system of claim 6, wherein the bundled strands comprise twisted carbon nanotubes.

8. The multi-modality imaging system of claim 1, wherein the carbon nanotube conductors comprise layered strands of carbon nanotube conductors.

9. The multi-modality imaging system of claim 1, wherein the carbon nanotube conductors comprise carbon nanotubes in a yarn-type configuration.

10. The multi-modality imaging system of claim 1, further comprising one or more capacitors coupled to the one or more MR RF coils using a conductive epoxy.

11. A multi-modality imaging system comprising:
    a first modality having one or more carbon nanotube conductors shaped and sized for operation in MR imaging; and
    a second modality configured to transmit radiation through or detect radiation that passes through the one or more carbon nanotube conductors, wherein the carbon nanotube conductors are configured to allow ionizing radiations to pass therethrough.

12. The multi-modality imaging system of claim 11, wherein the radiation comprises X-ray radiation transmitted from an X-ray radiation source of the radiation scanning portion.

13. The multi-modality imaging system of claim 11, wherein the radiation comprises gamma radiation emitted as gamma rays from a patient.

14. The multi-modality imaging system of claim 11, wherein the first modality comprises a Magnetic Resonance Imaging (MRI) scanner and the second modality comprises one of a Computed Tomography (CT) scanner, a Positron Emission Tomography (PET) scanner, a Single-Photon Emission Computed Tomography (SPECT) scanner, a radiotherapy system, or an X-ray fluoroscopy system.

15. The multi-modality imaging system of claim 11, wherein the carbon nanotube conductors comprise carbon nanotube based ballistic conductors.

16. The multi-modality imaging system of claim 11, wherein the carbon nanotube conductors comprise bundled strands of twisted carbon nanotube conductors.

17. The multi-modality imaging system of claim 11, wherein the carbon nanotube conductors comprise layered strands of carbon nanotube conductors.

18. The multi-modality imaging system of claim 11, wherein the carbon nanotube conductors comprise carbon nanotubes in a yarn-type configuration.

19. A method for forming Magnetic Resonance (MR) Radio-Frequency (RF) coils, the method comprising:
    forming carbon nanotube structures having MR imaging properties;
    forming a carbon nanotube conductor arrangement from the carbon nanotube structures; and
    forming MR RF coils from the carbon nanotube conductor arrangement for use in a multi-modality imaging system having (i) a Magnetic Resonance (MR) scanning portion configured to acquired MR data of a patient using the MR RF coils and (ii) a radiation potion configured to transmit radiation through or detect radiation from the patient, wherein the carbon nanotube conductors are configured to allow ionizing radiations to pass therethrough.

\* \* \* \* \*